United States Patent [19]

Delton et al.

[11] Patent Number: 4,504,368

[45] Date of Patent: Mar. 12, 1985

[54] ALKALI METAL ION-SELECTIVE COMPOSITIONS AND ELEMENTS AND A METHOD OF USING SAME

[75] Inventors: Mary H. Delton, Honeoye Falls; Daniel S. Daniel, Rochester, both of N.Y.

[73] Assignee: Eastman Kodak Company, Rochester, N.Y.

[21] Appl. No.: 514,744

[22] Filed: Jul. 18, 1983

[51] Int. Cl.$^3$ .............................................. G01N 27/30
[52] U.S. Cl. ..................... 204/1 T; 204/418; 260/330; 260/330.3; 260/330.6; 549/352; 549/353
[58] Field of Search ...................... 204/417, 418, 1 A; 549/352, 353; 260/330, 330.3, 330.6

[56] References Cited

U.S. PATENT DOCUMENTS

| | | | |
|---|---|---|---|
| 3,579,541 | 5/1971 | Chang .......................... | 549/353 X |
| 3,591,604 | 7/1971 | Yale et al. .................... | 260/330 |
| 3,644,346 | 2/1972 | Cusic et al. .................. | 260/330 X |
| 3,987,061 | 10/1976 | Pedersen ..................... | 260/340.2 |
| 4,214,968 | 7/1980 | Battaglia et al. ............. | 204/418 |
| 4,276,141 | 6/1981 | Hawkins ...................... | 204/418 |
| 4,361,473 | 11/1982 | Young et al. ................. | 204/418 |

OTHER PUBLICATIONS

E. Pretsch et al., Research/Development Magazine, vol. 25, No. 3, pp. 20–23, Mar. 1974.
Shiga et al., Chemistry Letters, pp. 1021–1022, 1980.
Aoki et al., Chemistry Letters, pp. 1583–1584, 1981.
Pedersen, J.A.C.S., 89(26), pp. 7017–7036, (1967).

Primary Examiner—G. L. Kaplan
Attorney, Agent, or Firm—J. Lanny Tucker

[57] ABSTRACT

Ion-selective compositions which comprise an ionophore, a compound capable of solvating the ionophore and a supporting matrix are disclosed. The ionophores useful in these compositions are certain crown ethers. These ion-selective compositions are particularly useful in ion-selective membranes and electrodes which are capable of selectively transporting a first ion in preference to a second ion. Such compositions, membranes and electrodes are useful for potentiometric measurement of alkali metal ions, e.g. lithium, sodium and potassium, in aqueous solutions, e.g. biological fluids. Dry-operative electrodes using these ion-selective compositions as membranes are also disclosed.

22 Claims, No Drawings

ALKALI METAL ION-SELECTIVE COMPOSITIONS AND ELEMENTS AND A METHOD OF USING SAME

FIELD OF THE INVENTION

This invention relates to compositions which are useful as ion-selective membranes. In particular, it relates to novel ion-selective compositions useful as ion-selective membranes which are capable of selectively transporting a first ion in preference to a second ion. These membranes are useful in ion-selective electrodes of various types.

BACKGROUND OF THE INVENTION

In the diagnosis and treatment of various diseases as well as in preventative health checkups, it is becoming increasingly important to monitor the concentrations of certain ions in a patient's body. Ions which have merited considerable attention in the diagnosis and treatment of heart disease, manic depressive psychosis, diabetes, hypertension and kidney disease are the alkali metal cations, e.g. lithium, sodium and potassium.

A great variety of electrodes and devices for the measurement of such cations in solutions are known. Usually, they include a reference electrode and a separate ion-selective electrode. When these two electrodes are simultaneously immersed in the same sample of a solution containing such ions, a potential develops across a membrane between the electrodes, which potential is proportional to the concentration of the ion to which the ion-selective electrode is sensitive. Frequently, it is desirable to measure the concentration of one ion in preference to other ions which may be in a solution. In that case, the ion-selective composition of the ion-selective electrode must be capable of selectively transporting the first ion across the membrane in preference to all other ions. An electrode having this capability is often referred to in the art as an ion-selective electrode.

One type of ion-selective electrode has an electrode body (usually a glass container) containing a reference solution in contact with a half-cell of known potential (a reference electrode) and an ion-selective glass membrane located in an aperture in the electrode body. The ion-selective membrane is mounted in such a fashion that, when the electrode is immersed in the unknown solution, the membrane contacts both the reference and unknown solutions. A metal probe coated with a layer of insoluble salt of the metal in the reference solution and immersed therein serves as one of the contacts for measuring the potential between the electrodes and provides a reference potential for the electrode. The sensitivity of the electrode to an ion in solution is determined by the composition of the glass membrane. This type of electrode is referred to in the art as a "barrel" electrode.

In addition to glass membranes, polymeric ion-selective membranes are also known. These membranes generally comprise a polymeric binder or support as a supporting matrix which is impregnated with a solution of an ion-selective carrier in a carrier solvent. The ion-selective carrier is a compound which is capable of sequentially complexing the desired ion, transporting the ion through the composition and releasing the ion. This compound is also referred to in the art as an "ionophore" or "ion carrier". Depending upon the ionophore, solvent and binder, membranes of this type can be used to detect a particular ion preferentially to other ions which may be in the solution.

A significant advance in the ion-selective-electrode art is the dry-operative electrode described in U.S. Pat. No. 4,214,968 (issued July 29, 1980 to Battaglia et al). Prior to the discovery of such dry-operative ion-selective electrodes, electrodes had to be either stored in an aqueous solution or treated with an aqueous solution just prior to use in an ion-activity-determining operation. The term "dry-operative" refers to an ion-selective electrode which provides reproducible potentiometric determination of ion activity which is related to the ion concentration of an aqueous test solution with no requirement for wet storage or preconditioning prior to use.

One of the specific ion-selective electrodes disclosed in the examples of the Battaglia et al patent is a sodium ion-selective electrode using methyl monensin as the sodium-selective ionophore. While methyl monensin is a useful ionophore for some ion-selective membranes and electrodes, still further improvements, particularly in the selectivity of the electrode for one cation over another, are desired. For example, methyl monensin is useful in the determination of sodium in blood serum because blood serum usually contains a relatively high level of sodium compared to the competing ion potassium. However, a higher degree of selectivity of sodium over potassium is needed for the determination of sodium in urine and some other biological fluids (e.g. intracellular fluids containing red blood cells) because urine and those fluids either have widely fluctuating concentrations of potassium and sodium ions, or have more potassium ions than sodium ions.

In other instances, it is desirable to selectively determine the potassium ion concentration in biological fluids which may contain a variety of other cations, including sodium. Where the concentrations of those other cations (e.g. sodium) are high in comparison to potassium ion concentration, or where the potassium ion concentration widely fluctuates, a high degree of selectivity of potassium over sodium is desired.

Crown ethers are well known ion-complexing compounds. They complex, for example, with alkali and alkaline earth metal ions, ammonium ions and others. Many crown ethers, however, are not adequately selective to particular ions. An ionophore must be capable, not only of selectively complexing an ion from the solution, but also of transporting the ion across the membrane and then decomplexing the ion into the solution on the other side of the membrane. For example, Example 51 of the Battaglia et al patent mentioned hereinabove describes the use of two crown ethers, 1,5,9,13-tetramethyl-1,5,9,13-tetranonyl tetrafuro-16-crown-4-ether and dicyclohexyl-12-crown-4-ether, as ionophores in dry-operative ion-selective electrodes. Either unacceptable electrode drift or poor ion selectivity, particularly to lithium ions, was exhibited by those crown ethers. Hence, crown ethers are not necessarily the preferred ionophores for use in ion-selective electrodes where severe accuracy, precision, ion selectivity and reproducibility requirements exist.

The preparation and testing of several azo-containing crown ether dyes are described in Shiga et al *Chemistry Letters*, pp. 1021–1022, 1980, entitled "Azo-Crown Ethers. The Dyes with the Azo Group Directly Involved in the Crown Ether Skeleton"; and Aoki et al, *Chemistry Letters*, pp.1583–1584, 1981, entitled "Ion- Dipole Association Chromatography on Ion Exchanger in Non-Aqueous Media. Separation and Characterization of Crown Ethers and Related Compounds". The first article describes how alkali metal ions were ion-pair extracted from an aqueous solution into benzene using the azo crown ether dyes and tetrabromophenolphthalein ethyl ester as a pairing anion at pH 9. According to the teaching of this reference, the dye

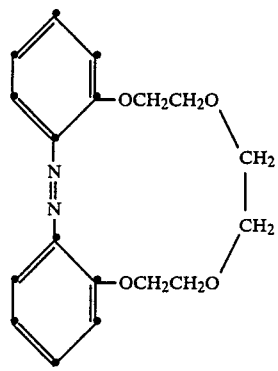

I.

extracts Na+ (along with the pairing ion) preferably to K+ from an aqueous solution into benzene. The second article describes the use of an ion-exchange column containing various ions to study the ion complexation characteristics of the same azo crown ether dyes. A dye similar to (I) but having one less —OCH₂CH₂— group in the crown backbone is described in this reference as having a slight preferential affinity for Na+ over tetramethylammonium, Li+ or K+ ions.

The Shiga et al reference teaches that particular crown ether dyes can extract alkali metal ions with a pairing anion from water into benzene. Such extraction data, however, does not suggest that the described dyes would be useful as ionophores in ion-selective electrodes. Generally, such paired extraction compounds, if incorporated into ion-selective electrodes, would severely limit the utility of those electrodes by reducing their sensitivity to cations. Because the capability of a compound to act as an ionophore is not predictable from ion extraction or ion complexation data, there is no suggestion in these references that the described dyes would be useful as ionophores in ion-selective electrodes to assay selectively for certain cations.

Hence, there is a need in the art for new ion-selective compositions and electrodes which are highly selective for certain cations (e.g. Na+ or K+) and can be used to assay selectively for those cations in solutions containing a variety of such ions in fluctuating or disproportionate concentrations.

SUMMARY OF THE INVENTION

It has been found that a certain class of crown ethers are particularly useful as ionophores in sodium and potassium ion-selective compositions. These compositions comprise a crown ether represented by the structure noted hereinbelow, a compound capable of solvating the crown ether, and a supporting matrix. The composition is useful as an ion-selective membrane and is capable of preferentially complexing a particular ion from solution, transporting the ion from one side of the membrane to the other side, and releasing the ion to a second solution. This selectivity is particularly useful in determining sodium or potassium ion concentrations in solutions which either contain widely fluctuating amounts of both ions or high concentrations of the ion not desired to be assayed. With use of the compositions and electrodes of this invention, interference of one ion with the measurement of another can be greatly reduced.

In accordance with the present invention, there is provided a composition comprising (a) a crown ether represented by the structure

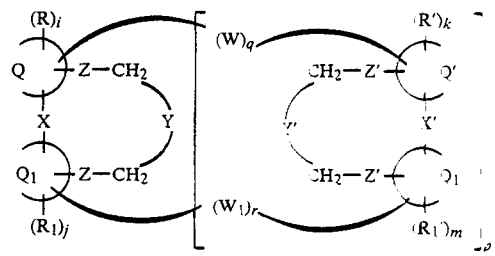

wherein
p is 0 or 1; when p is 1, q and r are independently 0 or 1, and when p is 0, q and r are both 0; X and X' are independently azo, azoxy, azomethine, vinylene, sulfoxyl, oxydimethylene, ureylene or iminodicarbonyl;

Y and Y' independently represent a bond or a linking group having the carbon, sulfur, nitrogen or oxygen atoms necessary to complete a crown ring backbone having up to 29 atoms;

Z and Z' are independently oxy, methyleneoxy, imino, amido or oxycarbonyl;

R, R₁, R' and R₁' are independently alkyl, aryl, cycloalkyl, a heterocycle, alkoxy, amino, acylamino, amido, keto, carbamoyl, carboxy, alkoxycarbonyl, cyano, halo or nitro or another substituent group having up to 60 carbon, sulfur, nitrogen or oxygen atoms in the backbone;

i, j, k and m are independently zero or a positive integer up to a number such that Q, Q₁, Q' or Q₁' is fully substituted, respectively;

Q, Q₁, Q' and Q₁' are independently the atoms necessary to complete a 5- to 14-membered mono- or polycyclic ring; and W and W₁ are independently linking groups having up to 60 carbon, sulfur, nitrogen or oxygen atoms in the backbone; (b) a compound capable of solvating the crown ether; and (c) a hydrophobic binder.

This composition is useful as an ion-selective membrane. In preferred embodiments, the solvating compound is a hydrophobic carrier solvent.

The compositions described above are also useful in ion-selective electrodes. Thus, in another aspect of the present invention, there is provided an ion-selective electrode having an ion-selective composition comprising an ionophore which is the crown ether described hereinabove, a compound capable of solvating the crown ether, and a supporting matrix.

The compositions described herein are also useful in dry-operative ion-selective electrodes. Thus, in still another aspect of the present invention there is provided a dry-operative ion-selective electrode comprising the crown ether ionophore described hereinabove dissolved in a compound capable of solvating the crown ether.

Further still, this invention provides a method for determining the concentration of a cation in a specimen sample. This method comprises physically contacting the specimen sample with the ion-selective electrode described hereinabove.

DETAILED DESCRIPTION OF THE INVENTION

We have discovered that certain crown ethers are useful ionophores in ion-selective compositions and electrodes. "Crown ethers" in a term generally ascribed to cyclic polyethers, the first of which were reported by C. J. Pedersen in J.A.C.S., 89(26), pp. 7017–7036 (1967). Generally, these compounds contain from about 9 to about 60 atoms in the ring backbone including from about 3 to about 20 oxygen or other Group VIA atoms in the ring backbone. The size of the ring is generally sufficiently large so that an ion can be complexed in the center of the ring.

The crown ethers useful in the practice of the present invention are represented by the structure

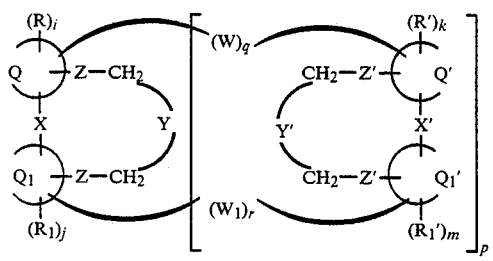

wherein p is 0 or 1, and preferably 0; when p is 0, q and r are both 0, and when p is 1, q and r are independently 0 or 1; X and X' are independently azo

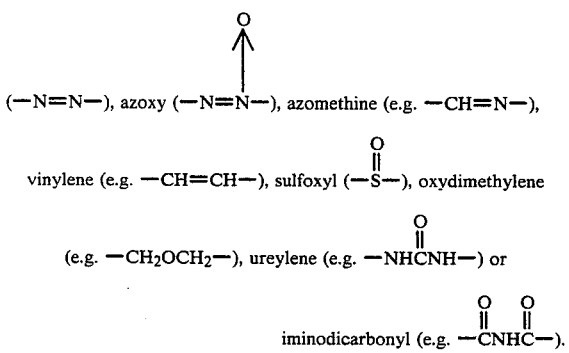

If desired, the hydrogen atoms on any of these linkage groups can be replaced by an alkyl group (e.g. having 1 to 6 carbon atoms, substituted or unsubstituted, branched or straight-chain); an aryl group (e.g. phenyl or naphthyl, substituted or unsubstituted); a cycloalkyl group (e.g. 5–7 carbon atoms, substituted or unsubstituted); or a heterocyclic group having 5 to 7 atoms in the ring (e.g. pyridyl or furyl).

Preferably, X and X' are independently azo, azoxy, azomethine or vinylene. More preferably, both are the same and are azo, azoxy or azomethine, and compounds having such linkages are generally termed azo crown ethers. Most preferably, X and X' are azo.

In the structure illustrated hereinabove, Y and Y' are independently a bond linking the two illustrated methylene groups or a linking group having the carbon, sulfur, nitrogen or oxygen atoms necessary to complete a crown ring backbone having up to 29 atoms, and preferably from about 13 to about 19 atoms. Generally, Y and Y' are independently one or more aromatic, aliphatic or heterocyclic units. Where Y or Y' has more than one of such aromatic, aliphatic or heterocyclic units, those units can be linked together with one or more oxy, azo, thio or sulfoxyl and other linkages as defined for X and X' hereinabove. Such units can have up to 20 carbon atoms in the backbone, and preferably have from 1 to 15 carbon atoms for the aliphatic units, from 6 to 14 carbon atoms for the aromatic units, and from 5 to 14 atoms in the heterocyclic units.

For example, Y and Y' can independently comprise one or more alkylene, arylene, cycloalkylene, alkylene-oxy-alkylene, alkylene-oxy-arylene, arylene-oxy-arylene, alkylene-sulfoxyl-alkylene, arylene-alkylene-oxy-alkylene, cycloalkylene-oxy-alkylene, oxy-alkylene-oxy, oxy-cycloalkylene-oxy, arylene-azo-arylene, arylene-azomethine-arylene, alkylene-amino-alkylene, alkylenethio-alkylene and the like groups linked together with one or more oxy, thio, azo or sulfoxyl linkages. Such linked groups can be unsubstituted, or substituted in a manner as described hereinabove for X and X'. Examples of Y and Y' groups include:

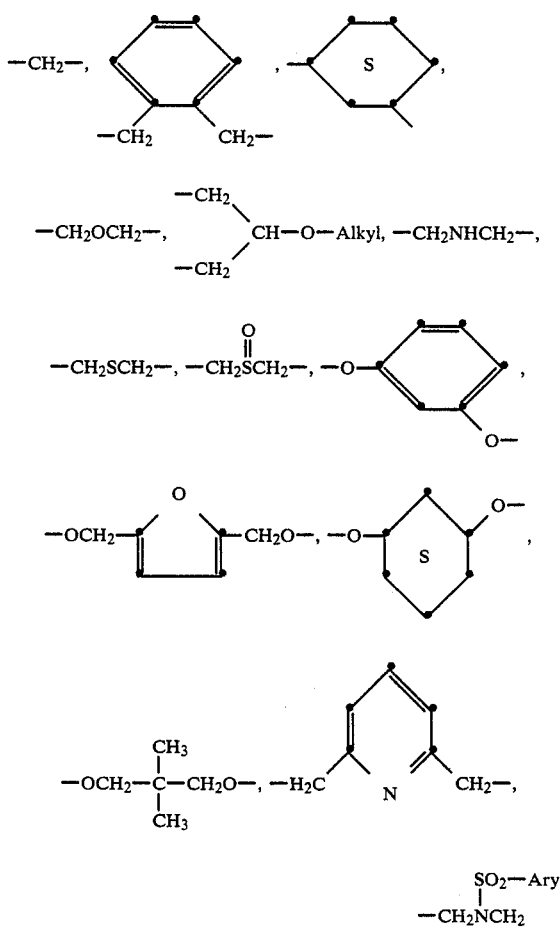

and the like.

Y and Y' can also be

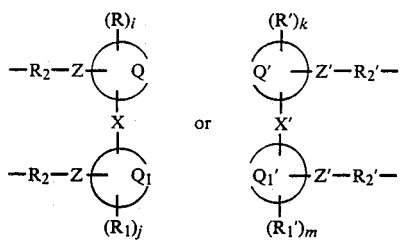

wherein $R_2$ and $R_2'$ are independently alkylene having 1 to 20 carbon atoms in the backbone (branched, straight-chain, substituted or unsubstituted) and can be interrupted with one or more oxy or thio groups. Preferably, $R_2$ and $R_2'$ are independently alkylene-oxy-alkylene, such as methylene-oxy-methylene, ethylene-oxy-methylene and the like.

Preferably, Y and Y' are independently $-(\text{alkylene-oxy-alkylene})_n-$ wherein n is an integer of 1 to 8, and more preferably, an integer of 1 to 3.

Z and Z' are independently oxy (—O—), methyleneoxy (—CH$_2$O—), imino (—NH—), amido

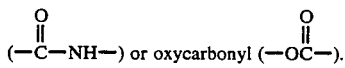

Preferably, each is oxy or methyleneoxy. The methyleneoxy can be substituted, if desired, with lower alkyl having 1 to 4 carbon atoms (e.g. methyl, ethyl, n-propyl, isopropyl, etc.).

In the above-identified crown ether structure, Q, $Q_1$, Q' and $Q_1'$ are independently the atoms (e.g. carbon, oxygen, nitrogen, sulfur, selenium, etc.) necessary to complete a 5- or 14-membered mono- or polycyclic ring (e.g. aromatic carbocyclic or heterocyclic ring). Examples of aromatic carbocyclic rings include phenylenes and naphthylenes and fused ring compounds (including those with saturated side rings). Examples of heterocyclic rings include pyran, pyrazine, pyridine, pyridazine, pyrazolone, thiophene, imidazole, thiazole, triazine, quinoline, benzothiazole and the like.

Preferably, Q, $Q_1$, Q' and $Q_1'$ are independently aromatic carbocyclic rings having from 6 to 10 carbon atoms, (e.g. phenylenes and naphthalenes).

One or more of the hydrogen substituents of any or all of Q, $Q_1$, Q' and $Q_1'$ can be replaced by R, $R_1$, R' and $R_1'$ groups, respectively. This is represented in the above-identified crown ether structure by $(R)_i$, $(R_1)_j$, $(R')_k$ and $(R_1')_m$ respectively wherein i, j, k and m are independently zero or a positive integer of up to a number such that Q, $Q_1$, Q' and $Q_1'$ is fully substituted, respectively (e.g. i, j, k or m could be an integer up to 10). Preferably, i, j, k and m are independently 1 or 2.

Useful R, $R_1$, R' and $R_1'$ groups include alkyl, preferably of 1 to 12 carbon atoms (unsubstituted or substituted, e.g. methyl, ethyl, isopropyl, hexyl, chloromethyl, benzyl, etc.); aryl, preferably of from 6 to 14 carbon atoms (unsubstituted or substituted e.g. phenyl, xylyl, tolyl, alkoxyphenyl, nitrophenyls, naphthyls, etc.); cycloalkyl, preferably of from 5 to 14 carbon atoms (unsubstituted or substituted, e.g. cyclopentyl, cyclohexyl, methylcyclohexyl, halocycloheptyls, etc.); a heterocyclic group, preferably of 5 to 10 atoms as described hereinabove for Q and $Q_1$ (e.g. pyridyl, quinolyl, thiazolyl, etc.); alkoxy, preferably of from 1 to 20 carbon atoms (unsubstituted or substituted, e.g. methoxy, ethoxy, propoxy, isoproproxy, t-butoxy, n-heptyloxy, etc.); amino (mono- or dialkyl amino); acyl-amino; amido; keto; carbamoyl; carboxy; alkoxycarbonyl, preferably of from 2 to 20 carbon atoms (unsubstituted or substituted, e.g. methoxycarbonyl, isopropoxycarbonyl, etc.); cyano; halo (e.g. fluoro, chloro, bromo and iodo); or nitro.

In addition, any of R, $R_1$, R' and $R_1'$ can be a substituent having up to 60 carbon, sulfur, nitrogen or oxygen atoms in the backbone. Generally, such groups include one or more aliphatic, aromatic or heterocyclic units as defined hereinabove for Y and Y', which units are linked together with oxy, azo, thio, sulfoxyl, oxycarbonyl or other linkages known in the art.

Any of the above-defined R, $R_1$, R' and $R_1'$ groups can contain one or more ion-coordinating sites which will coordinate with an alkali metal ion. Such sites can be at the end of the R, $R_1$, R' and $R_1'$ group or anywhere along its backbone. Examples of such coordinating sites are alkoxy, carbamoyl, amido, thio and others known in the art.

W and $W_1$ are independently linking groups having up to 60 carbon, sulfur, nitrogen or oxygen atoms in the backbone, and generally from about 3 to about 20 of such atoms in the backbone. These linking groups exist only if p is 1. Generally, W and $W_1$ are independently one or more aliphatic, aromatic or heterocyclic units which can be linked together with oxy, azo, thio, sulfoxyl, oxycarbonyl or other linkages known in the art, as defined for Y and Y' hereinabove. Alternatively, W and $W_1$ can each be an ureylene, iminodicarbonyl or similar linking group having at least 3 atoms in the backbone. Preferably, W and $W_1$ are the same linking group.

Crown ethers useful in the practice of this invention include:

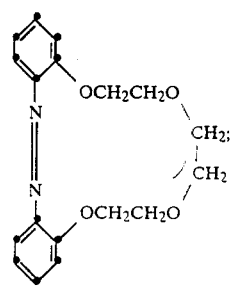

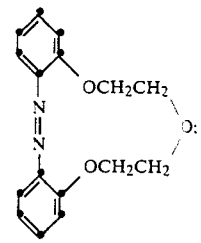

I.

-continued
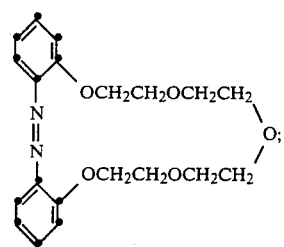 III.
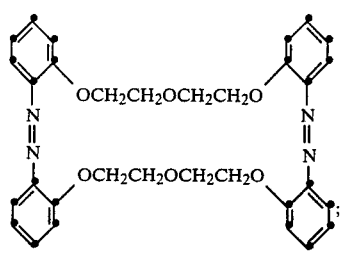 IV.
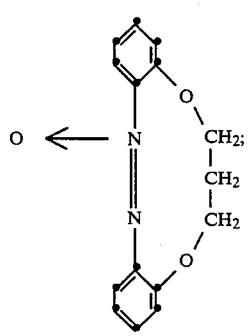 V.
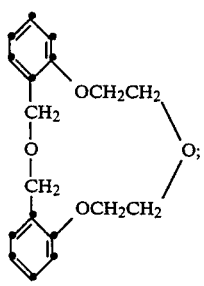 VI.
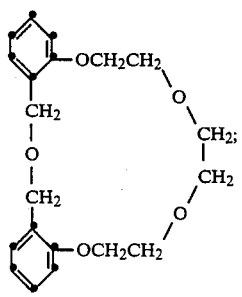 VII.
-continued
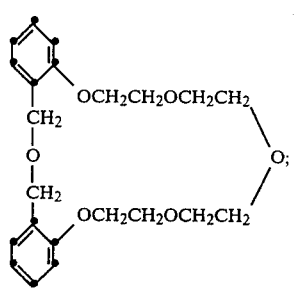 VIII.
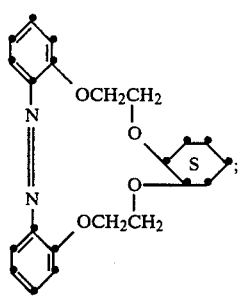 IX.
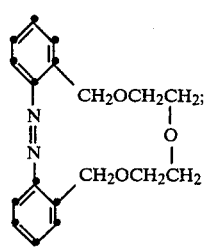 X.
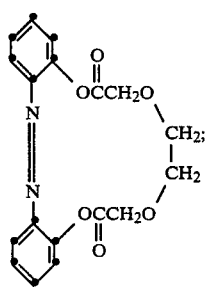 XI.
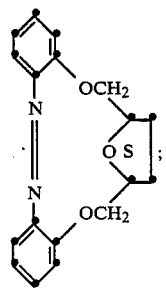 XII.

XIII. 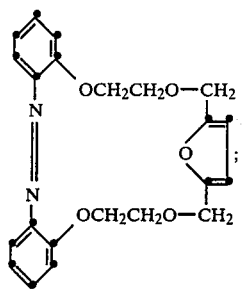
XIV. 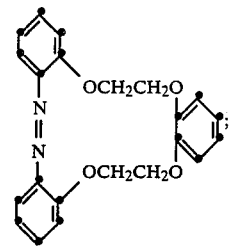
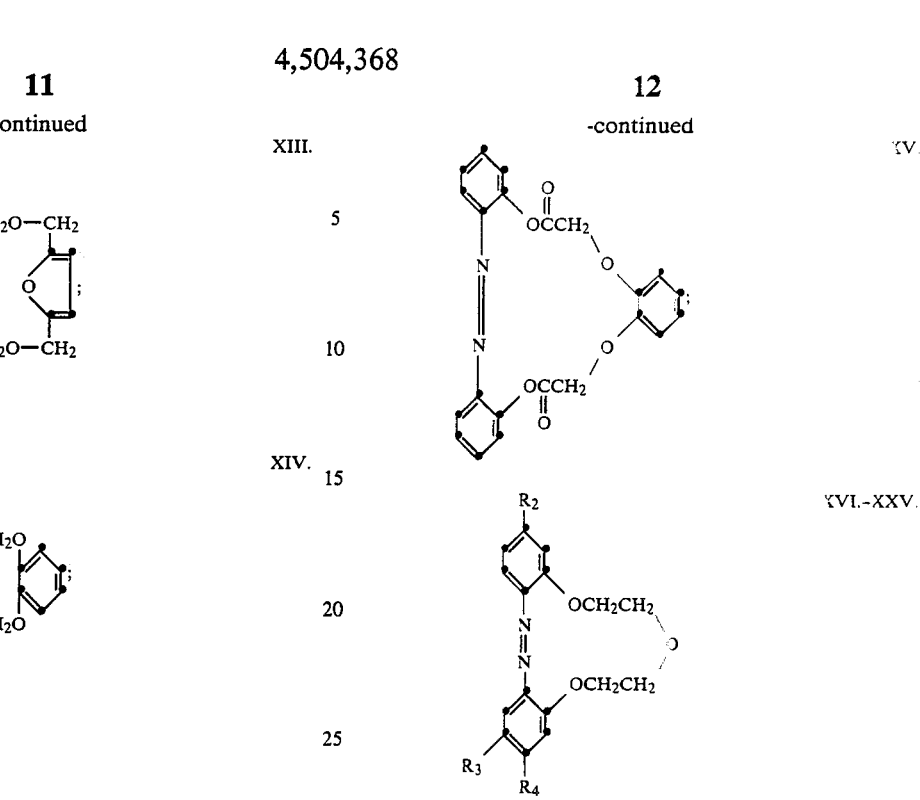
XVI.-XXV.
wherein $R_2$, $R_3$ and $R_4$ are defined as follows:
|  | $R_2$ | $R_3$ | $R_4$ |
|---|---|---|---|
| XVI | —H | —CH$_3$ | —H |
| XVII | —H | —H | —N(CH$_3$)$_2$ |
| XVIII | —NO$_2$ | —CH$_3$ | —H |
| XIX | —OCH$_3$ | —CH$_3$ | —H |
| XX | —OCH$_3$ | —H | —N(CH$_3$)$_2$ |
| XXI | —H | —OCH$_3$ | —H |
| XXII | —OCH$_3$ | —OCH$_3$ | —H |
| XXIII | —H | —OCH$_3$ | —OCH$_3$ |
| XXIV | —OCH$_3$ | —OCH$_3$ | —OCH$_3$ |
| XXV | —H | —COOCH$_2$CH$_3$ | —H |
XXVI. 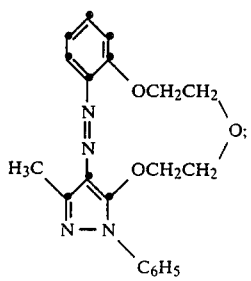
XXVII. 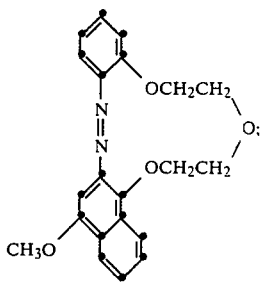

|        | R₂ | R₃ | R₄ |
|--------|----|----|----|
| XXVIII. | 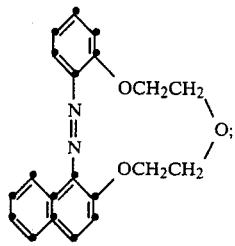 | | |
| XXIX.   | 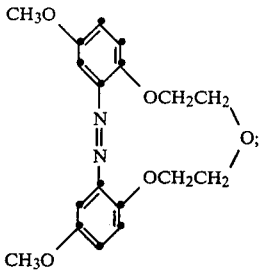 | | |
| XXX.    | 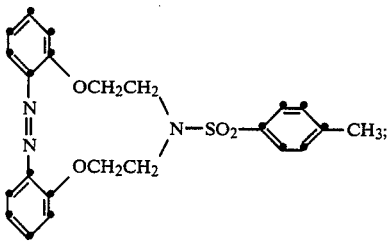 | | |
| XXXI.   | 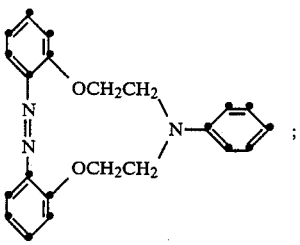 | | |
| XXXII.  | 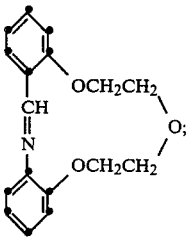 | | |
| XXXIII. | 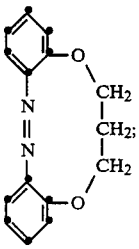 | | |

|     | R₂ | R₃ | R₄ |
|-----|----|----|----|
| XXXIV. | 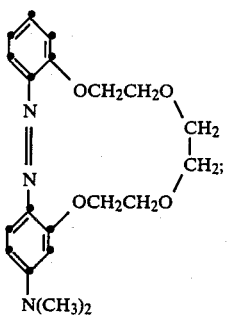 | | |
| XXXV. | 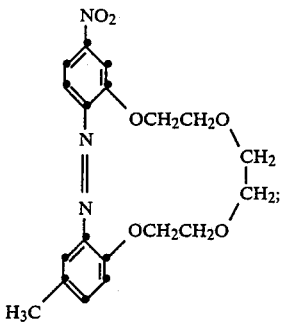 | | |
| XXXVI. | 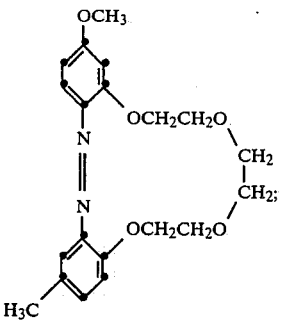 | | |
| XXXVII. | 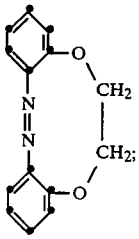 | | |
| XXXVIII. | 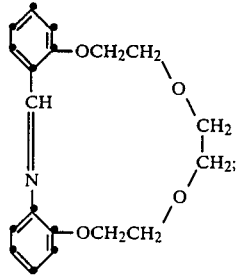 | | |

| | $R_2$ | $R_3$ | $R_4$ |
|---|---|---|---|

-continued

XXXIX.

XL.

XLI.

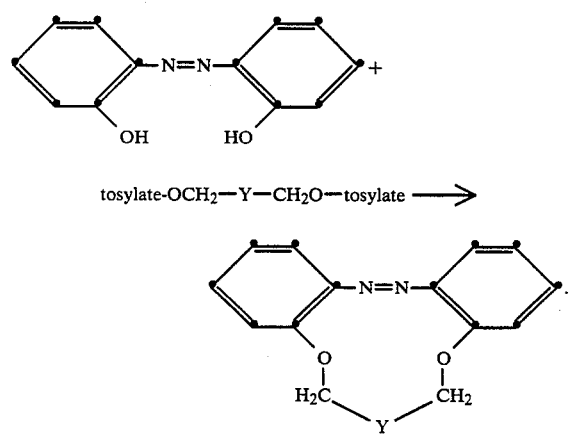

The crown ethers useful in the practice of this invention can be prepared by two general procedures. One procedure consists of condensing the appropriate diphenol with the ditosylate of the appropriate glycol. For example, azo crown ethers I, II, III, IV, XXX and XXXI are prepared according to the following general equation:

The second general procedure consists of cyclizing the appropriate phenol to the azo crown ether as in the preparation of crown ethers XVI-XXIX and XXXIV-XXXVI. This procedure can be illustrated by the following general equation:

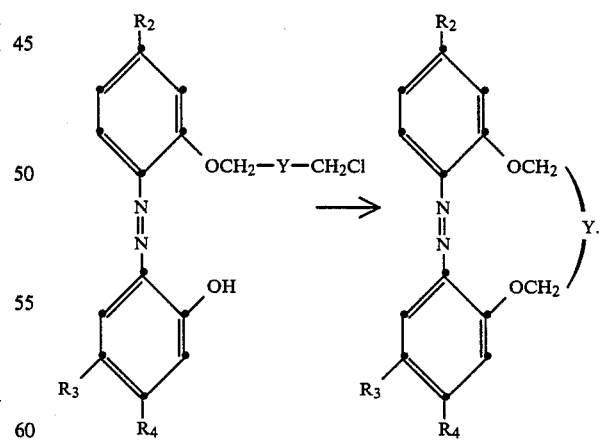

The details of the preparation of several crown ethers useful in this invention are given hereinbelow prior to the Examples.

In addition to the crown ethers described hereinabove, the compositions of the present invention include a compound which is capable of solvating the crown ether. Solvation is necessary so that the ion is transported through the membrane by the solvated crown ether. In some embodiments, one or more polymeric binders which are capable of solvating the crown ether are used. If a polymer is capable of dissolving, at least partially, the crown ether, it is useful in this embodiment. Exemplary polymers which are so useful are described in U.S. Pat. No. 3,419,634 (issued Dec. 31, 1968 to Vaughn, Jr.). The preparation of ion-selective membranes using these solvating polymers is described in U.S. Pat. No. 3,743,588 (issued July 3, 1973 to Brown, Jr. et al). In these embodiments, the polymer functions as both the compound which is capable of solvating the crown ether and the supporting matrix for the composition.

In other and preferred embodiments, the crown ether is solvated by one or more separate organic solvents and the supporting matrix is a separate component. Such a matrix must allow for the transport of the ion which is bound to the crown ether in the organic solvent. For example, a porous glass support is useful as the supporting matrix. In these embodiments, the crown ether is dissolved in the organic solvent and the resulting solution is imbibed into the porous glass support to provide an ion-selective membrane. In other and preferred embodiments, the solution of the crown ether is dispersed in a hydrophobic binder, e.g. a hydrophobic polymer binder. By "hydrophobic" is meant substantially water-insoluble. The binder dispersion is coated and dried to produce an ion-selective membrane according to the present invention.

Where a separate solvent is used to solvate the crown ether, the solvent can be any of a wide variety of solvents, provided that it is capable of at least partially dissolving the crown ether. The solvent (often referred to in the art as a carrier solvent) provides ion mobility in the membrane. If a hydrophobic binder is used as the supporting matrix, the solvent must be compatible with the binder. Useful carrier solvents are hydrophobic organic solvents including phthalates, sebacates, aromatic and aliphatic ethers, phosphates, mixed aromatic aliphatic phosphates, adipates, nitrated ethers or esters and mixtures of these solvents. Particularly useful solvents include dibutyl sebacate, bromophenyl phenyl ether, triisodecyl trimellitate, bis(2-ethylhexyl) sebacate, o-nitrophenyl valerate, bis(2-ethylhexyl) 4-nitrophthalate, dimethyl phthalate, diisodecyl phthalate, dioctyl phenylphosphonate, o-nitrophenyl phenyl ether, 2-nitrophenyl octyl ether, o-nitrophenyl octyl ether and tris(2-ethylhexyl) phosphate. Diisodecyl phthalate is a preferred solvent.

If the crown ether is included in a carrier solvent as described above, a membrane is formed using a dispersion of the solvent-crown ether in one or more binders as the supporting matrix. Useful binders include hyrophobic natural or synthetic polymers capable of forming thin films of sufficient permeability to produce, in combination with the crown ether and carrier solvent, ionic mobility across the membrane. Useful polymers include poly(vinyl chloride); poly(vinylidene chloride); poly(acrylonitrile); polyurethanes, particularly aromatic polyurethanes; copolymers of vinyl chloride and vinylidene chloride; poly(vinyl butyral); poly(vinyl formal); poly(vinyl acetate); copolymers of vinyl acetate and vinyl alcohol; silicone elastomers; and copolymers of vinyl alcohol, cellulose esters and polycarbonates. Other useful polymers include carboxylated polymers of poly(vinyl chloride) and mixtures and copolymers of such materials. Membranes including these binders, the crown ethers and the carrier solvents described hereinabove are prepared using conventional film-coating or casting techniques.

The membranes of the present invention can contain the described components over a wide range of concentrations or coverages. The coverage of crown ether depends upon the particular crown ether used and the compound used to solvate it, as well as other factors. The preferred membrane comprise a hydrophobic binder having the solvent and crown ether dispersed therein. In these membranes, crown ether coverages of between about 0.1 $g/m^2$ and 2.0 $g/m^2$ are useful and coverages between 0.2 $g/m^2$ and 0.8 $g/m^2$ are preferred.

The carrier solvent is present in an amount sufficient to solvate the crown ether. The amount therefore depends on the particular solvent and crown ether chosen. Generally, more solvent is used than is necessary to solvate the crown ether so that it remains solvated under a variety of storage conditions. A 100 to 500 percent excess on a weight basis is useful. Usually, the coverage of carrier solvent will be within the range of about 2 $g/m^2$ to about 24 $g/m^2$.

The amount of hydrophobic binder which is present is determined by the desired thickness of the membrane and by the necessity for providing support for the crown ether-solvent dispersion. The memranes generally have a thickness in the range of from about 2 $\mu$m to about 20 $\mu$m. The binder coverage is usually between about 2 $g/m^2$ and 24 $g/m^2$, and preferably from about 3 to about 12 $g/m^2$.

In addition to the binder, crown ether and solvent, the compositions of the present invention optionally contain other components such as surfactants and plasticizers in amounts known to those skilled in the art.

Surfactants are useful components of the described membranes. The surfactants serve a variety of functions including improving the coatability of the membrane composition and improving the solvation of the crown ether by the binder or solvent. Useful surfactants include nonionic surfactants such as the alkylaryl polyether alcohols (Tritons TM) available from Rohm and Haas Co; (p-isononylphenoxy)polyglycidol (Surfactant 10G TM) available from Olin Mathieson Corp; polyoxyethylene (20) oleyl ether (Brij 98 TM), polyoxyethylene sorbitan monolaurate (Tween 20 TM) and Span 80 TM, all available from Atlas Chemical Industries; poly(-dimethyl-co-methylphenyl siloxane) (DC-510 TM) available from Dow Corning; Zonyl FSN TM available from E. I. duPont; and fluorochemical surfactant FC134 TM available from 3M Co.

A useful ion-selective electrode comprises:
  (a) a reference electrode in physical contact with
  (b) a reference composition which is, in turn, in physical contact with one side of
  (c) an ion-selective membrane of the type described hereinabove.

In one embodiment, the ion-selective electrode is in the form of a glass tube. The ion-selective membrane forms the bottom of the tube. The tube is at least partially filled with a salt solution of known concentration forming the reference composition. Immersed in the reference composition is a reference electrode which is a metal electrode having a thin metal salt layer on its outer surface. The ion-selective electrode is used by immersing at least the membrane of the electrode in the unknown solution. One side of a voltmeter is connected to the reference electrode immersed in the reference composition and the other side is connected to a conducting probe in the unknown solution. The potential which develops across the voltmeter is proportional to the difference in ion concentration between the unknown solution and the reference composition.

As noted, the membranes of the present invention are useful in a variety of electrode structures. For example, the membranes of the present invention are useful in place of, or in addition to, the glass ion-selective membrane of a conventional barrel-type electrode. Useful electrodes of this type are disclosed, for example, in U.S. Pat. Nos. 3,598,713, 3,502,560, 3,562,129, 3,691,047, 3,753,887, 3,833,495, 3,671,414 and 3,743,588. The membranes are also useful in the ion-selective electrodes described in Japanese Patent Publications 17851/1982 and 17852/1982, both published Jan. 29, 1982, and particularly in the dry ion-selective electrodes described therein.

In particularly preferred embodiments, the compositions of the present invention are useful in dry-operative ion-selective electrodes as described in U.S. Pat. No. 4,214,968 (issued to Battaglia et al) noted hereinabove. In these embodiments, there is provided a dry-operative ion-selective electrode including:

(a) a dried internal reference element comprising the dried residue of a solution of a salt and a hydrophilic polymeric binder in a solvent for the polymer and the salt and, (b) in physical contact with the reference element, a hydrophobic ion-selective membrane of predetermined uniform thickness in regions thereof intended for physical contact with a liquid sample for analysis, the memberane comprising a hydrophobic binder having distributed therein a crown ether ionophore, as described hereinabove, dissolved in a carrier solvent. In this embodiment of the present invention, the electrodes are made by a process using components which are described in U.S. Pat. No. 4,214,968, the disclosure of which is hereby incorporated by reference in its entirety. As used throughout this specification and in the claims, the expressions "dry-operative", "dried" and "uniform" have the meanings defined in the Battaglia et al patent.

The membranes and electrodes of this invention can be used to selectively determine the concentration of a cation, such as an alkali metal ion (e.g. lithium, sodium, potassium, etc.), in specimen samples, e.g. in an aqueous solution, e.g. biological fluids such as blood sera and urine or suspension of tissue. Generally, a portion of such a sample is brought into physical contact with the electrode (e.g. a dry ion-selective electrode) described hereinabove which is capable of making potentiometric measurements related to the alkali metal ion concentration. Subsequently, the difference in potential between the portion of specimen sample and the reference electrode is measured. Preferably, a drop of the specimen sample is spotted onto the ion-selective membrane of such electrode by hand or machine or other suitable dispensing means, but other ways of contacting the electrode with the sample are acceptable.

PREPARATION OF CROWN ETHERS

Some of the crown ethers described herein were prepared using the procedures described hereinbelow. All solvents used in the following preparations were reagent grade unless otherwise specified. Dimethylformamide was dried over 4A molecular sieves before use. Potassium t-butoxide was sublimed before use. All reactions were run under an argon atmosphere. All products were characterized by elemental analyses as well as infrared, nuclear magnetic resonance and mass spectra using conventional equipment, and all spectra were consistent with the described structures.

Crown ethers II and IV were prepared in the following manner. About 200 ml of tetrahydrofuran (dried over 5A molecular sieves) and 6.4 g (57 mmol) of potassium t-butoxide were added to 6 g (28 mmol) of 2,2'-azodiphenol in a 500 ml flask. The resulting deep red-colored solution was brought to reflux and a solution of 11.6 g (28 mmol) of diethyleneglycol ditosylate in 150 ml of tetrahydrofuran was added dropwise over a period of 18–24 hours. After two hours of ditosylate addition, a precipitate of potassium tosylate was evident. Refluxing was continued for an additional 24 hours. The reaction mixture was then cooled and suction filtered through a pad of Celite TM, and the tetrahydrofuran was removed under vacuum. The resulting dark red viscous oil was chromatographed on silica gel and eluted with dichloromethane until the first yellow band was eluted. It was then eluted with successively more polar mixtures of ethyl acetate-$CH_2Cl_2$ until the final red-orange band of crown ether IV was eluted. Fractions were then monitored by thin layer chromatography (5% ethyl acetate-$CH_2Cl_2$ and 10% methanol-$CHCl_3$). In this manner, 2.3 g of crown ether II (29% yield) were obtained as a reddish-orange syrup and 0.4 g (10% yield, m.p. 161°–162° C.) of crown ether IV were obtained as an orange solid. Some fractions contained both crown ethers. Those fractions were treated with warm hexane in which crown ether II was solubilized and filtered free of crown ether IV.

Crown ether I was prepared in a manner similar to that used to prepare crown ether II using 6 g (28 mmol) of 2,2'-azodiphenol and 12.8 g (28 mmol) of triethyleneglycol ditosylate. Crown ether I was obtained as a dark red oil which hardened to a solid (3.3 g, 36% yield, m.p. 58°–60° C.). This hardened material consisted of both cis and trans isomers.

Crown ether III was similarly prepared from 6 g (28 mmol) of 2,2'-azodiphenol and 14 g (28 mmol) of tetraethyleneglycol ditosylate, yielding 3.7 g (35.5% yield, m.p. 97°–102° C.). The product was isolated after filtration and solvent removal by trituration in boiling hexane a dozen times.

Crown ether XIX was prepared in the following manner. Crown ethers XVI–XVIII and XX–XXV were similarly prepared.

Preparation of 5-methoxy-2-nitrophenol:

A solution of resorcinol monomethyl ether (50 g, 0.4 mol) in glacial acetic acid (50 mL) was cooled to −10° C. and added dropwise over 3.5 hours to a cooled (−15° C.), stirred solution of fuming nitric acid (33 mL, 0.76 mol) in 150 mL of glacial acetic acid. The temperature was maintained between −10° and −15° C. by controlling the rate of addition. The resulting thick, red-black slush was then mixed with 400 mL of crushed ice and stirred for one hour. The mixture was then extracted with ether (2×400 mL), concentrated under reduced pressure, and the residue was steam distilled to give 32.1 g (47% yield) of a yellow solid. Recrystallization from methanol gave product having a m.p. of 92°–93° C.

Preparation of the Tosylate of 2-(2-chloroethoxy)ethanol:

A stirred solution of tosyl chloride (38 g, 0.2 mol) in 100 mL of Karl Fischer grade pyridine (in a 250 mL Erlenmeyer flask provided with a drying tube) was cooled to −10° C. in an ice/methanol bath. A solution of 2-(2-chloroethoxy)ethanol (25 g, 0.2 mol) in 30 mL of pyridine was added to the tosyl chloride solution. After 20 minutes, the reaction flask was refrigerated overnight. The resulting product was isolated by pouring the cold mixture onto 700 g of ice, stirring for one hour, and extracting the resulting oil into ether, yielding 45.1 g (81% yield) of a light yellow liquid.

Preparation of 5-methoxy-2-nitro[2-(2-chloroethoxy)ethoxy]benzene:

The sodium salt of 5-methoxy-2-nitrophenol (19.1 g, 0.1 mol) and the above chlorotosylate (27.8 g, 0.1 mol) were dissolved in 800 mL of dimethylformamide and heated on a steam bath with stirring for 16 hours. The resulting mixture was poured onto 800 mL of ice and the product obtained was extracted into ether. Purification by flash chromatography (45 × 60 mm, $CH_2Cl_2$) afforded 17 g (66% yield) of light yellow oil.

Preparation of Amine Hydrochloride:

5-Methoxy-2-nitro-[2-(2-chloroethoxy)-ethoxy]benzene (6.62 g, 0.024 mol) was dissolved in methanol (100 mL) in a Parr flask, and 200 mg of 10% Pd/C were added together with concentrated HCl (2.1 mL, 0.024 mol). The resulting mixture was hydrogenated at room temperature for 3 hours. After filtration through a Celite ™ pad, the methanol was removed under reduced pressure. The crude product thus obtained was dissolved in a minimum amount of methanol and treated with 1L of anhydrous ether with cooling to give the amine hydrochloride (5.6 g, 83% yield).

Diazotization of the Amine Hydrochloride:

A solution of the amine hydrochloride (2.26 g, 8 mmol) in 8 mL of water and 0.8 mL (9.28 mmol) of concentrated HCl were cooled in an ice bath. A cold solution of 8 mmol of sodium nitrite in 6 mL water was added portionwise over 5 minutes and the cold diazonium solution was used immediately in the next step.

Preparation of Azo compound:

The cold diazonium solution of the preceeding step was added dropwise to a stirring solution of p-cresol (0.84 g, 7.8 mmol) in 6.4 mL of 10% NaOH and 6 mL of water at 0° C. A reddish-brown oil separated as the reaction proceeded and after 15 minutes, the mixture was acidified to pH 4–5 with dilute HCl and extracted with $CH_2Cl_2$. Chromatography on 200 g of silica gel, eluting with $CH_2Cl_2$ gave 1.46 g (51% yield) of product (m.p. 83°–85° C.).

Preparation of Crown Ether XIX:

A mixture of 2.4 mmol of the azo compound prepared in the preceeding step, one equivalent of potassium t-butoxide and 160 mg of sodium iodide in 600 mL of dimethylformamide in a one-liter vessel was heated with stirring at 130° C. for 8 hours. When all the starting material had been reacted, the dimethylformamide was removed, and the residue was extracted with an ether—$CH_2Cl_2$ mixture. The resulting crown ether was purified by chromatography and the product obtained as a red oil.

Crown ether XXVII was prepared using the following procedure. Crown ethers XXVI and XXVIII were prepared similarly using the appropriate reactants.

Preparation of 2-nitro[2-(2-chloroethoxy)ethoxy]benzene:

This compound was prepared in a manner analogous to the preparation of 5-methoxy-2-nitro-[2-(2-chloroethoxy)ethoxy]benzene for crown ether XIX, except that the sodium salt of o-nitrophenol was used instead of the sodium salt of 5-methoxy-2-nitrophenol.

Preparation of the Amine Hydrochloride:

The above nitro intermediate was reduced using the method as described in the preparation of crown ether XIX.

Diazotization of the Amine Hydrochloride:

Diazotization was accomplished as in the preparation of crown ether XIX.

Preparation of Azo Compound:

The cold diazonium solution (8 mmol) prepared in the preceeding step was used immediately by adding it dropwise to a stirring solution of 4-methoxy-1-naphthol (1.39 g, 8 mmol) in 6.8 mL of 10% NaOH and 6 mL of water at 0° C. The resulting azo product crystallized out as the reaction proceeded. The mixture was acidified to pH 4–5 with acetic acid and the solid obtained was recrystallized from an acetic acid/water mixture to give 2.68 g (84% yield, m.p. 108°–109° C.).

Preparation of Crown Ether XXVII:

To 1.2 g (3 mmol) of the above azo compound in 1 L of dimethylformamide was added 336 mg (3 mmol) of potassium t-butoxide and 200 mg of sodium iodide. This mixture was stirred and heated at 130° C. for 7 hours and then the solvent was removed under reduced pressure. The resulting red semisolid was dissolved in 50 mL of $CH_2Cl_2$ and added to 500 mL of anhydrous ether. The crude azo crown ether mixed salt complex precipitated as a mustard-colored powder. After filtration, the azo crown was recovered from the complex by partitioning between water and $CH_2Cl_2$. Removal of the $CH_2Cl_2$ left a viscous oil. Purification by flash chromatography ($CH_2Cl_2$, followed by 1:1 $CH_2Cl_2$/ethyl acetate) gave pure crown ether XXVII in 51% yield.

Crown ethers V and XXXIII were prepared in the following manner.

A solution of 1,3-dichloropropane (11.3 g, 0.1 mol) and the sodium salt of o-nitrophenol (32.2 g, 0.05 mol) in 250 mL of dimethylformamide in a 500 mL flask was stirred at 130° C. for about 16 hours. After cooling the solution, it was poured into 1 L of ice and water with rapid stirring. After 2 hours at 0° C., the resulting mustard-colored solid was filtered and recrystallized from methanol (1 L) to give 22.2 g (70% yield) of colorless needles of 1,3-bis(o-nitrophenoxy)propane. A sample of this product (3.12 g, 9.8 mmol) was mixed with sodium hydroxide (1.5 g), lithium hydroxide (1.5 g), methanol (40 mL), tetrahydrofuran (100 mL) and water (100 mL) in a 500 mL flask. This solution was brought to reflux with vigorous stirring, and zinc dust (6 g, 0.09 mol) was added in portions over 2 hours. After further refluxing for about 10 hours, the solution was cooled, filtered to remove the zinc; and the tetrahydrofuran and methanol were removed under reduced pressure. The residual aqueous suspension of red-orange oil was extracted with ether/$CH_2Cl_2$ providing a red syrup (2.6 g) which was purified by gravity chromatography eluting with $CH_2Cl_2$. Thin layer chromatography indicated the presence of both crown ethers V and XXXIII. Further chromatography on silica gel with 20% ethyl acetate in hexane gave pure products: V as a yellow solid, 950 mg (36%), m.p. 76°–77° C., and XXXIII as a red-orange oil, 380 mg (15% yield).

Crown ethers VI–VIII were prepared in the following manner. 2,2'-Dihydroxybenzylether was prepared according to the procedure described by Sprung and Gladstone in *J. Amer. Chem. Soc.*, 71, 2907 (1949), and converted to its dianion with two equivalents of potassium t-butoxide in tetrahydrofuran. The appropriate ditosylate was added to the refluxing dianion solution dropwise over 16 hours. After a total reaction time of 45 hours, the reaction mixture was cooled, filtered and concentrated. Purification by chromatography on silica gel gave the desired products. The m.p. for compounds VI–VIII were 95°–97° C., 67°–78° C., and 87°–89° C., respectively.

Crown ether XXXII was prepared in the following manner. Salicylaldehyde was condensed with o-aminophenol in ethanol to yield 2,2'-azomethinediphenol. This compound was condensed with the appropriate ditosylate in tetrahydrofuran for 53 hours in the presence of potassium t-butoxide and the resulting yellow product was purified by chromatography to yield a yellow foam.

Crown ether XL was prepared in the following manner.

The starting material, 4',4''-dimethoxy-m-dibenzoylbenzene, was synthesized according to the procedure described by Weiss and Chledowski in Monatsh 65, 357 (1935) and subsequently reduced using the Huang-Minlon modification of the Wolff-Kishner reaction to provide 4',4''-dimethoxy-m-dibenzylbenzene as a viscous oil. Demethylation was carried out in an acetic acid/hydrobromic acid mixture at reflux for 7 hours. The 4',4''-dihydroxy-m-dibenzylbenzene (m.p. 138°–139° C.) was separated from contaminating partially reduced and/or partially hydrolyzed materials by chromatography on silica gel, eluting with increasingly polar mixtures of ethyl acetate in $CH_2Cl_2$.

Two equivalents of the amine hydrochloride (noted hereinabove) which was used to prepare crown ether XXVII was diazotized and slowly added to one equivalent of the above-described xylylene bis-phenol in dilute sodium hydroxide. The crude, solid xylylene bis (azophenol) thereby formed was purified by chromatography on silica gel to provide pure material as a viscous red oil that slowly solidified (62% yield, m.p. 80°–82° C.). This bis(azophenol) was cyclized to the bis(azo crown) ether in the same manner as used for the preparation of XXVII (noted hereinabove). The crude azo crown mixed salt complex that resulted was partitioned between $CH_2Cl_2$ and water, and the evaporated organic layer was extracted with ether and hexane to give crown ether XL as a red foam (40% yield).

In the following Examples, ion-selective electrodes were prepared using a variety of the crown ethers described hereinabove. The electrodes were of the format and were prepared by the methods described in the Battaglia et al patent noted hereinabove. The electrode comprised a polyester support having thereon, in sequence: a silver/silver chloride reference electrode; an electrolyte layer comprising gelatin (3–6 g/m²), NaCl (1.5–3.5 g/m²), glycerol (0.25–0.4 g/m²) and Olin Surfactant 10G ™ (0.3–0.9 g/m²); and a membrane layer. This membrane layer contained a binder comprising 1.8% carboxylated poly(vinyl chloride) (3–6 g/m²), a carrier solvent as indicated (4–8 g/m²), the crown ether as indicated (0.1–0.3 g/m²), and the surfactant DC-510 ™ (0.03–0.09 g/m²).

A Corning digital readout potentiometer was used to determine potentials. The electomotive force values were taken 3 minutes after contact with the test solutions. Activity coefficients were calculated as described by Bates and Altease in "Ion Selective Electrodes" (R. Durst, Ed.), Nat. Bur. of Stand. Spec., Publ. 314, Washington, D.C., 1969.

The following examples are provided to illustrate the practice of this invention.

EXAMPLE 1

Ion-Selective Electrode Using Crown Ether I As Ionophore

An ion-selective electrode was prepared containing crown ether I as ionophore and tested for ion selectivity using various carrier solvents. In the Shiga et al reference noted hereinabove, it was reported that crown ether I has an aqueous solution to benzene extraction coefficient of 4.18 for sodium ion and 2.77 for potassium ion. This example of our invention indicates, however, that crown ether I is highly selective for $K^+$ over $Na^+$.

Crown ether I and a carrier solvent were incorporated into a membrane layer of the ion-selective electrode described hereinabove. The electrode was tested by spotting 10 μL aliquots of solutions containing 0.05, 0.1, 0.15 or 0.3M sodium chloride and 0.1M KCl onto samples of the electrode. Potentials were measured against a silver/silver chloride electrode. The potential developed for each aliquot was plotted against the concentration of sodium in the aliquot. The result was a Nernstian slope in the range of $10^{-4}$ to $10^{-1}$M sodium for each experiment.

The selectivity coefficient (k) for $K^+$ was calculated (sodium being defined as one) using the potential data from the KCl aliquot. The results are shown in Table I below. Valinomycin was used as the ionophore in a control electrode. These results indicate that, contrary to the teaching of Shiga et al, crown ether I is more selective to $K^+$ over $Na^+$ when used in the described electrode.

TABLE I

| Ionophore | Carrier Solvent | $k\,K^+/Na^+$ |
|---|---|---|
| Crown ether I | triisodecyl trimellitate | 0.00173 |
| Crown ether I | bis(2-ethylhexyl) sebacate | 0.00175 |
| Crown ether I | diisodecyl phthalate | 0.00129 |
| Valinomycin | triisodecyl trimellitate | 0.000159 |

EXAMPLE 2

Use of Crown Ether II As Ionophore

Ion-selective electrodes were prepared using crown ether II as the ionophore in a manner like that described hereinabove. The ion selectivity of samples of these electrodes were evaluated by spotting 10 mL aliquots of solutions containing 0.05, 0.1, 0.15 or 0.3M sodium chloride and 0.1M potassium chloride, lithium chloride, ammonium chloride, calcium chloride or magnesium chloride onto the samples. The results are summarized in Table II below. A control electrode was also prepared using methyl monesin as the ionophore.

In the Aoki et al reference noted hereinabove, crown ether II is described as having only a slight preference for $Na^+$ over tetramethylammonium ion, $Li^+$ and $K^+$ in an ion exchange column. The data of this Example, however, indicates an unexpected and significant selectivity of this crown ether for $Na^+$ over $K^+$ and other cations when used in an ion-selective electrode according to this invention.

TABLE I

| Ionophore | Carrier Solvent | $Na^+/K^+$ | $Na^+/Li^+$ | $Na^+/NH_4^+$ | $Na^+/Ca^{++}$ | $Na^+/Mg^{++}$ |
|---|---|---|---|---|---|---|
| Crown Ether II | Bis(2-ethylhexyl) sebacate | 0.16 | 0.025 | 0.07 | 0.011 | 0.003 |
| Crown Ether II | 2-Nitrophenyl octyl ether | 0.022 | 0.007 | 0.008 | 0.008 | 0.002 |
| Methyl Monensin | Bis(2-ethylhexyl) sebacate | 0.56 | 0.35 | 0.12 | 0.008 | 0.004 |

EXAMPLE 3

Use Of Crown Ether IV As Ionophore

Ion-selective electrodes were prepared in a manner as described hereinabove, using crown ether IV as the ionophore. The ion selectivity of samples of these electrodes were also evaluated according to the procedure described in Example 2. The results are summarized in Table III below.

TABLE III

| Carrier Solvent | $Na^+/K^+$ | $Na^+/Li^+$ | $Na^+/NH_4^+$ | $Na^+/Ca^{++}$ | $Na^+/Mg^{++}$ |
|---|---|---|---|---|---|
| Bis(2-ethylhexyl)sebacate | 0.46 | 0.006 | 0.14 | 0.005 | 0.0005 |
| 2-Nitrophenyl-octyl ether | 0.3 | 0.01 | 0.16 | 0.01 | 0.001 |

EXAMPLE 4

Use Of Various Crown Ethers As Ionophores

Ion-selective electrodes were prepared in a manner as described hereinabove using various crown ethers as ionophores and various carrier solvents. The ion selectivities of samples of these electrodes were also evaluated according to the procedure described in the previous Examples. The results are summarized in Tables IV and V below.

TABLE IV

| Ionophore | k $Na^+/K^+$ BEHS* | NPOE** | DIDP*** |
|---|---|---|---|
| II | 0.16 | 0.022 | 0.022 |
| XVI | 0.029 | 0.013 | 0.017 |
| XVIII | 0.014 | 0.021 | 0.069 |
| XIX | 0.014 | 0.016 | 0.011 |
| XX | 0.83 | 0.74 | NA |
| XXI | NA | NA | 0.012 |
| XXII | NA | NA | 0.011 |
| XXIII | NA | NA | 0.021 |
| XXIV | NA | NA | 0.032 |
| XXV | NA | NA | 0.053 |
| XVIII + XIX (equimolar) | NA | NA | 0.016 |
| XXVII | NA | NA | 0.011 |
| XXVIII | 0.013 | 0.03 | 0.012 |
| XII | 0.46 | 0.17 | NA |
| XXIX | NA | NA | 0.014 |
| XL | NA | NA | 0.018 |
| XLI | NA | NA | 0.011 |

*bis(2-ethylhexyl) sebacate
**2-nitrophenyl octyl ether
***diisodecyl phthalate
NA = not available

TABLE V

| Ionophore | k $K^+/Na^+$ BEHS* | NPOE** | DIDP*** | k $Na^+/Li^+$ BEHS* | NPOE** |
|---|---|---|---|---|---|
| I | 0.00175 | 0.0022 | 0.00129 | NA | NA |
| XXXIV | 0.04 | 0.005 | NA | NA | NA |
| XXXV | 0.0013 | 0.0015 | NA | NA | NA |
| XXXVI | 0.05 | 0.003 | NA | NA | NA |
| XXXVII | 0.278 | 0.042 | NA | 2.3 | 2.0 |
| XXXIII | 0.244 | 0.213 | NA | 0.2 | 0.1 |
| III | 0.11 | 0.05 | NA | 0.009 | 0.03 |
| VI | 0.21 | 0.097 | NA | NA | NA |
| VII | 0.46 | 0.2 | NA | NA | NA |
| VIII | 0.058 | 0.024 | NA | 0.038 | 0.093 |
| XIV | 0.021 | 0.0092 | NA | 0.076 | 0.09 |
| XXX | 0.217 | 0.067 | NA | 0.78 | 1.48 |
| XXXI | 0.385 | 0.625 | NA | 0.42 | 1.37 |
| XXXII | 0.769 | 2.44 | NA | 0.51 | NA |
| XXXIII | 0.24 | 0.21 | NA | 0.2 | 0.1 |
| XXVI | NA | NA | 0.167 | NA | NA |

*bis(2-ethylhexyl) sebacate
**2-nitrophenyl octyl ether
***diisodecyl phthalate
NA = not available While the invention has been described in detail with particular reference to preferred embodiments thereof, it will be understood that variations and modifications can be effected within the spirit and scope of the invention.

We claim:

1. A composition comprising:
   (a) a crown ether containing one or more ether linkages and represented by the structure:

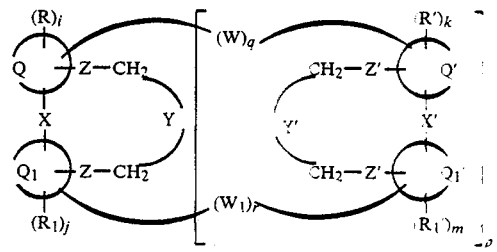

wherein p is 0 or 1; when p is 1, q and r are independently 0 or 1, and when p is 0, q and r are both 0; X and X' are independently azo, azoxy, azomethine, vinylene, sulfoxyl, oxydimethylene, ureylene or iminodicarbonyl;

Y and Y' independently represent a bond or a linking group having the carbon, sulfur, nitrogen or oxygen atoms necessary to complete a crown ring backbone having up to 29 atoms;

Z and Z' are independently oxy, methyleneoxy, imino, amido or oxycarbonyl;

R, $R_1$, R' and $R_1'$ are independently alkyl, aryl, cycloalkyl, a heterocycle, alkoxy, amino, acylamino, amido, keto, carbamoyl, carboxy, alkoxycarbonyl, cyano, halo or nitro or another substituent group having up to 60 carbon, sulfur, nitrogen or oxygen atoms in the backbone;

i, j, k and m are independently zero or a positive integer up to a number such that Q, $Q_1$, Q' or $Q_1'$ is fully substituted, respectively;

Q, $Q_1$, Q' and $Q_1'$ are independently the atoms necessary to complete a 5- to 14-membered mono- or polycyclic ring; and W and $W_1$ are independently linking groups having up to 60 carbon, sulfur, nitrogen or oxygen atoms in the backbone;

(b) a compound capable of solvating said crown ether; and (c) a hydrophobic binder.

2. The composition of claim 1 wherein said solvating compound is a hydrophobic carrier solvent.

3. The composition of claim 1 wherein p is 0; X is azo, azoxy, azomethine or vinylene;

Y is (alkylene-oxy-alkylene)$_n$ wherein n is an integer of 1 to 8;

Z is oxy or methyleneoxy;

R and $R_1$ are independently alkyl, alkoxy or nitro;

i and j are independently 1 or 2; and

Q and $Q_1$ are independently aromatic carbocyclic rings.

4. The composition of claim 3 wherein X is azo; n is an integer of 1 to 3; Z is oxy; and both Q and $Q_1$ are 6- to 10-membered aromatic carbocyclic rings.

5. A composition comprising:

(a) a crown ether represented by the structure

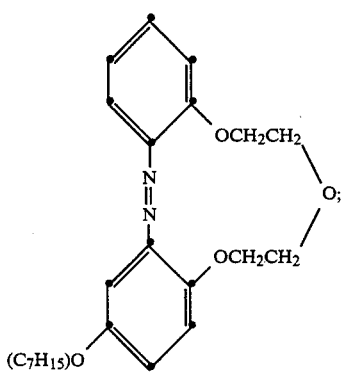

(b) a compound capable of solvating said crown ether; and (c) a hydrophobic binder.

6. The composition of claim 5 wherein said solvating compound is diisodecyl phthalate.

7. An ion-selective electrode having an ion-selective membrane composition comprising (a) an ionophore which is a crown ether containing one or more ether linkages and represented by the structure:

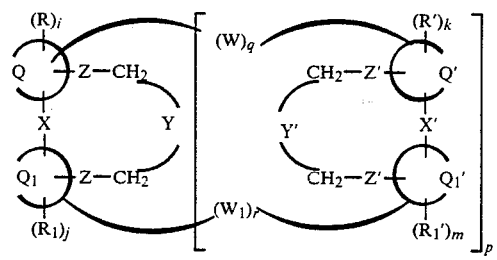

wherein p is 0 or 1; when p is 1, q and r are independently 0 or 1, and when p is 0, q and r are both 0; X and X' are independently azo, azoxy, azomethine, vinylene, sulfoxyl, oxydimethylene, ureylene or iminodicarbonyl;

Y and Y' independently represent a bond or a linking group having the carbon, sulfur, nitrogen or oxygen atoms necessary to complete a crown ring backbone having up to 29 atoms;

Z and Z' are independently oxy, methyleneoxy, imino, amido or oxycarbonyl;

R, $R_1$, R' and $R_1'$ are independently alkyl, aryl, cycloalkyl, a heterocycle, alkoxy, amino, acylamino, amido, keto, carbamoyl, carboxy, alkoxycarbonyl, cyano, halo or nitro or another substituent group having up to 60 carbon, sulfur, nitrogen or oxygen atoms in the backbone;

i, j, k and m are independently zero or a positive integer up to a number such that Q, $Q_1$, Q' or $Q_1'$ is fully substituted, respectively;

Q, $Q_1$, Q' and $Q_1'$ are independently the atoms necessary to complete a 5- to 14-membered mono- or polycyclic ring; and W and $W_1$ are independently linking groups having up to 60 carbon, sulfur, nitrogen or oxygen atoms in the backbone;

(b) a compound capable of solvating said crown ether; and (c) a supporting matrix.

8. The electrode of claim 7 wherein said solvating compound is selected from the group consisting of phthalates, sebacates, aromatic and aliphatic ethers, phosphates, mixed aromatic-aliphatic phosphonates, adipates, nitrated ethers or esters, and mixtures thereof.

9. The electrode of claim 7 wherein said supporting matrix is a hydrophobic binder.

10. The electrode of claim 7 comprising a surfactant.

11. A dry-operative ion-selective electrode comprising a crown ether ionophore dissolved in a compound capable of solvating said crown ether, said crown ether containing one or more ether linkages and represented by the structure:

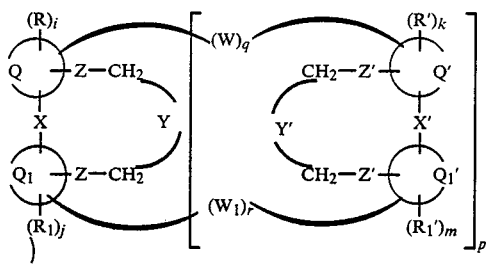
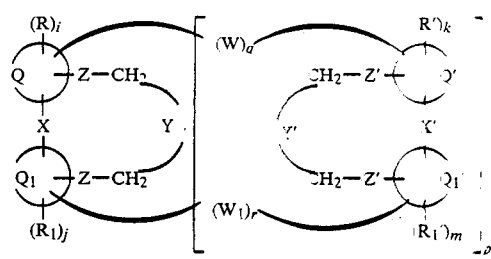

wherein p is 0 or 1; when p is 1, q and r are independently 0 or 1, and when p is 0, q and r are both 0; X and X' are independently azo, azoxy, azomethine, vinylene, sulfoxyl, oxydimethylene, ureylene or iminodicarbonyl;

Y and Y' independently represent a bond or a linking group having the carbon, sulfur, nitrogen or oxygen atoms necessary to complete a crown ring backbone having up to 29 atoms;

Z and Z' are independently oxy, methyleneoxy, imino, amido or oxycarbonyl;

R, $R_1$, R' and $R_1'$ are independently alkyl, aryl, cycloalkyl, a heterocycle, alkoxy, amino, acylamino, amido, keto, carbamoyl, carboxy, alkoxycarbonyl, cyano, halo or nitro or another substituent group having up to 60 carbon, sulfur, nitrogen or oxygen atoms in the backbone;

i, j, k and m are independently zero or a positive integer up to a number such that Q, $Q_1$, Q' or $Q_1'$ is fully substituted, respectively;

Q, $Q_1$, Q' and $Q_1'$ are independently the atoms necessary to complete a 5- to 14-membered mono- or polycyclic ring; and W and $W_1$ are independently linking groups having up to 60 carbon, sulfur, nitrogen or oxygen atoms in the backbone;

(a) a compound capable of solvating said crown ether; and (b) a supporting matrix.

12. The electrode of claim 11 wherein said ionophore and solvating compound are distributed within a hydrophobic binder.

13. A dry operative ion-selective electrode including:

I. a dried internal reference element comprising the dried residue of a solution of a salt and a hydrophilic polymeric binder in a solvent for said binder and said salt, and II. in physical contact with said reference element, a hydrophobic ion-selective membrane of predetermined uniform thickness in regions thereof intended for physical contact with a liquid sample for analysis, said membrane comprising a hydrophobic binder having distributed therein a crown ether ionophore containing one or more ether linkages and represented by the structure wherein p is 0 or 1; when p is 1, q and r are independently 0 or 1, and when p is 0, q and r are both 0; X and X' are independently azo, azoxy, azomethine, vinylene, sulfoxyl, oxydimethylene, ureylene or iminodicarbonyl;

Y and Y' independently represent a linking group having the carbon, sulfur, nitrogen or oxygen atoms necessary to complete a crown ring backbone having up to 29 atoms;

Z and Z' are independently oxy, methyleneoxy, imino, amido or oxycarbonyl;

R, $R_1$, R' and $R_1'$ are independently alkyl, aryl, cycloalkyl, a heterocycle, alkoxy, amino, acylamino, amido, keto, carbamoyl, carboxy, alkoxycarbonyl, cyano, halo or nitro or another substituent group having up to 60 carbon, sulfur, nitrogen or oxygen atoms in the backbone;

i, j, k and m are independently zero or a positive integer up to a number such that Q, $Q_1$, Q' or $Q_1'$ is fully substituted, respectively;

Q, $Q_1$, Q' and $Q_1'$ are independently the atoms necessary to complete a 5- to 14-membered mono- or polycyclic ring; and W and $W_1$ are independently linking groups having up to 60 carbon, sulfur, nitrogen or oxygen atoms in the backbone;

(a) a compound capable of solvating said crown ether; and (b) a hydrophobic binder.

14. The electrode of claim 13 wherein p is 0; X is azo, azoxy, azomethine or vinylene;

Y is (alkylene-oxy-alkylene)$_n$ wherein n is an integer of 1 to 8;

Z is oxy or methyleneoxy;

R and $R_1$ are independently alkyl, alkoxy or nitro;

i and j are independently 1 or 2; and

Q and $Q_1$ are independently aromatic carbocyclic rings.

15. The electrode of claim 14 wherein X is azo; n is an integer of 1 to 3; Z is oxy; and both Q and $Q_1$ are 6- to 10-membered aromatic carbocyclic rings.

16. The electrode of claim 13 wherein said ionophore has the structure

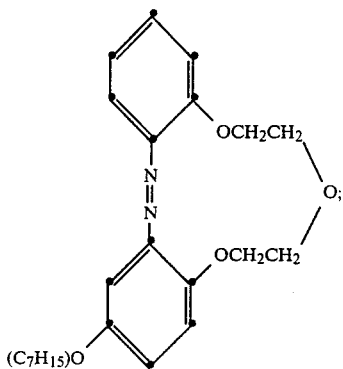

(b) a compound capable of solvating said crown ether; and (c) a hydrophobic binder.

17. The electrode of claim 13 wherein said carrier solvent is diisodecyl phthalate.

18. A method for determining the concentration of an alkali metal ion in a specimen sample, said method comprising physically contacting said sample with an electrode sensitive to said alkali metal ion, said electrode comprising a membrane composition sensitive to said alkali metal ion, said composition comprising:

(a) a crown ether ionophore containing one or more ether linkages and represented by the structure

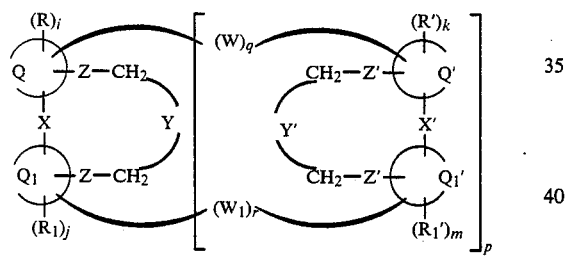

wherein p is 0 or 1; when p is 1, q and r are independently 0 or 1, and when p is 0, q and r are both 0; X and X' are independently azo, azoxy, azomethine, vinylene, sulfoxyl, oxydimethylene, ureylene or iminodicarbonyl;

Y and Y' independently represent a bond or a linking group having the carbon, sulfur, nitrogen or oxygen atoms necessary to complete a crown ring backbone having up to 29 atoms;

Z and Z' are independently oxy, methyleneoxy, imino, amido or oxycarbonyl;

R, $R_1$, R' and $R_1'$ are independently alkyl, aryl, cycloalkyl, a heterocycle, alkoxy, amino, acylamino, amido, keto, carbamoyl, carboxy, alkoxycarbonyl, cyano, halo or nitro or another substituent group having up to 60 carbon, sulfur, nitrogen or oxygen atoms in the backbone;

i, j, k and m are independently zero or a positive integer up to a number such that Q, $Q_1$, Q' or $Q_1'$ is fully substituted, respectively;

Q, $Q_1$, Q' and $Q_1'$ are independently the atoms necessary to complete a 5- to 14-membered mono- or polycyclic ring; and W and $W_1$ are independently linking groups having up to 60 carbon, sulfur, nitrogen or oxygen atoms in the backbone;

(b) a compound capable of solvating said crown ether; and (c) a hydrophobic polymer binder.

19. A method for determining the concentration of an alkali metal ion in a specimen sample, said method comprising the steps of:

A. bringing said sample into physical contact with a dry ion-selective electrode which is capable of making potentiometric measurements related to alkali metal ion concentration, said dry ion-selective electrode comprising:

I. a reference electrode in physical contact with

II. a reference composition which is in turn in physical contact with one side of III. a membrane composition sensitive to said alkali metal ion, said composition comprising:

(a) a crown ether ionophore containing one or more ether linkages and represented by the structure

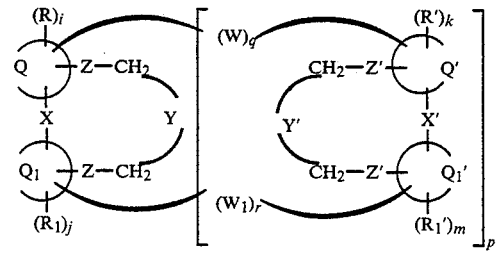

wherein p is 0 or 1; when p is 1, q and r are independently 0 or 1, and when p is 0, q and r are both 0; X and X' are independently azo, azoxy, azomethine, vinylene, sulfoxyl, oxydimethylene, ureylene or iminodicarbonyl;

Y and Y' independently represent a bond or a linking group having the carbon, sulfur, nitrogen or oxygen atoms necessary to complete a crown ring backbone having up to 29 atoms;

Z and Z' are independently oxy, methyleneoxy, imino, amido or oxycarbonyl;

R, $R_1$, R' and $R_1'$ are independently alkyl, aryl, cycloalkyl, a heterocycle, alkoxy, amino, acylamino, amido, keto, carbamoyl, carboxy, alkoxycarbonyl, cyano, halo or nitro or another substituent group having up to 60 carbon, sulfur, nitrogen or oxygen atoms in the backbone;

i, j, k and m are independently zero or a positive integer up to a number such that Q, $Q_1$, Q' or $Q_1'$ is fully substituted, respectively;

Q, $Q_1$, Q' and $Q_1'$ are independently the atoms necessary to complete a 5- to 14-membered mono- or polycyclic ring; and W and $W_1$ are independently linking groups having up to 60 carbon, sulfur, nitrogen or oxygen atoms in the backbone;

(b) a compound capable of solvating said crown ether; and (c) a hydrophobic polymer binder; and B. measuring the difference in potential between said specimen sample and said reference electrode.

20. An ion-selective electrode having an ion-selective membrane composition comprising
(a) an ionophore which is a crown ether represented by the structure

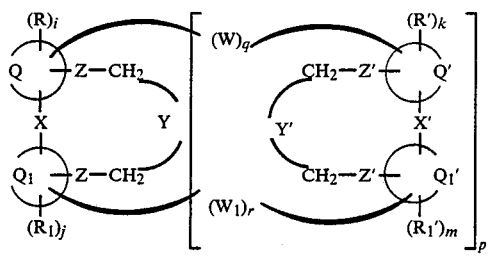

wherein p is 0; X is azo; Y is substituted or unsubstituted —alkylene-oxy-alkylene)$_n$ wherein n is an integer of 1 to 3; Z is oxy; R and R$_1$ are independently alkyl, aryl, cycloalkyl, a heterocycle, alkoxy, amino, acylamino, amido, keto, carbamoyl, carboxy, alkoxycarbonyl, cyano, halo or nitro or another substituent group having up to 60 carbon, sulfur, nitrogen or oxygen atoms in the backbone; i and j are independently zero or a positive integer up to a number such that Q or Q$_1$ is fully substituted, respectively; and Q and Q$_1$ are phenylene rings;

(b) a compound capable of solvating said crown ether; and (c) a supporting matrix.

21. The electrode of claim 20 which is potassium ion-selective and wherein said ionophore has said structure wherein n is 2.

22. The electrode of claim 20 which is sodium ion-selective and wherein said ionophore has said structure wherein n is 1.

* * * * *